US005383870A

United States Patent [19]

Takai et al.

[11] Patent Number: 5,383,870

[45] Date of Patent: Jan. 24, 1995

[54] LIQUID-PERMEABLE TOPSHEET FOR BODY FLUID ABSORPTIVE GOODS

[75] Inventors: Hisashi Takai; Tsutomu Kido, both of Kawanoe, Japan

[73] Assignees: Mitsui Petrochemical Industries, Ltd., Tokyo; Uni-Charm Corporation, Ehime, both of Japan

[21] Appl. No.: 114,839

[22] Filed: Sep. 2, 1993

[30] Foreign Application Priority Data

Sep. 7, 1992 [JP] Japan .................................. 4-238417

[51] Int. Cl.[6] ........................ A61F 13/15; A61F 13/20

[52] U.S. Cl. .................................... 604/378; 604/358; 604/366; 604/370; 604/384

[58] Field of Search ............... 604/358, 365, 366, 368, 604/370, 372, 374, 375, 378, 379, 380, 383, 384

[56] References Cited

U.S. PATENT DOCUMENTS

| | | | |
|---|---|---|---|
| 3,929,135 | 12/1975 | Thompson . | |
| 4,634,440 | 1/1987 | Widlund et al. | 604/385.1 |
| 4,634,440 | 1/1987 | Widlund . | |
| 4,781,962 | 11/1988 | Zamarripa et al. | 604/378 |
| 4,798,603 | 1/1989 | Meyer et al. | 604/378 |
| 4,892,532 | 1/1990 | Boman | 604/378 |
| 4,908,026 | 3/1990 | Sukiennik et al. | 604/378 |
| 5,037,409 | 8/1991 | Chen et al. | 604/378 |
| 5,078,710 | 1/1992 | Suda et al. | 604/366 |
| 5,135,521 | 8/1992 | Luceri et al. | 604/383 |
| 5,145,727 | 9/1992 | Potts et al. | 428/198 |
| 5,180,620 | 1/1993 | Mende . | |
| 5,188,625 | 2/1993 | Van Iten . | |
| 5,229,191 | 7/1993 | Austin . | |
| 5,264,268 | 11/1993 | Luceri et al. | 428/138 |

FOREIGN PATENT DOCUMENTS

| | | | |
|---|---|---|---|
| 351156 | 7/1979 | Austria . | |
| 0409535 | 1/1991 | European Pat. Off. . | |
| 0518340A1 | 12/1992 | European Pat. Off. . | |
| 3517640 | 11/1985 | Germany . | |
| 2180271 | 3/1987 | United Kingdom . | |
| 9114414 | 10/1991 | WIPO | 604/366 |
| 9309741 | 5/1993 | WIPO | 604/378 |

*Primary Examiner*—Randall L. Green
*Assistant Examiner*—P. Zuttarelli
*Attorney, Agent, or Firm*—Lowe, Price, LeBlanc & Becker

[57] ABSTRACT

A topsheet for body fluid absorptive articles improved so that liquid passages formed in the topsheet may be stabilized during use of the goods and the topsheet may offer cloth-like feeling and appearance, the topsheet being composed of an upper sheet layer made from melt blown nonwoven fabric containing downwardly extending liquid passageways and an underlying fibrous layer 11 bonded thereto adjacent the lower openings of said liquid passageways, whereby the liquid passageways will not be collapsed and the lower openings of these passageways will not be distorted.

6 Claims, 1 Drawing Sheet

LIQUID-PERMEABLE TOPSHEET FOR BODY FLUID ABSORPTIVE GOODS

BACKGROUND OF THE INVENTION

The present invention relates to a liquid-permeable topsheet used in disposable fluid absorptive goods such as sanitary napkins and disposable diapers.

Conventionally, disposable body fluid absorptive goods have often employed perforated plastic sheet or nonwoven fabric as material for a liquid-permeable topsheet thereof. In the case of perforated plastic sheet, the sheet is provided with liquid passages extending therethrough from top to bottom thereof and lower openings of the respective liquid passages are arranged in contact with an absorbent core so that excreted body fluids may be transferred rapidly into the absorbent core. Such technique is well known, for example, from Japanese Patent Publication No. 1982-17081 which discloses tapered liquid passages and Japanese patent application Disclosure Gazette No. 1985-259261 discloses cylindrical liquid passages. Use of nonwoven fabric, on the other hand, is preferred to use of a plastic sheet in that the nonwoven fabric offers soft feeling and therefore comfortableness for wearing.

While the conventional technique provides the above-mentioned advantages in its own way, use of the perforated plastic sheet has drawbacks often disliked by the consumer, particularly, slippery feeling and glossy appearance peculiar to the plastic sheet, so there is an acute demand for a topsheet improved to offer feeling as well as appearance similar to cloth as closely as possible. In the case where nonwoven fabric is used as material for the topsheet, the excreted body fluids can be transferred toward the absorbent core as rapidly as when the plastic sheet is used as the topsheet, but the nonwoven fabric falls short of the ability to maintain the top surface of the sheet dry after the body fluids have been transferred toward the absorbent core, i.e., short of a dry touch. In this regard, a proper improvement is demanded. To make the best use of the advantages provided by these conventional materials and compensate for the shortcomings thereof, it has already been proposed, for example, in Japanese patent application Disclosure Gazette No. 1991-51355 to employ a sheet of melt blown nonwoven fabric formed by subjecting thermoplastic fibres to a welding process. While the technique disclosed in this Disclosure Gazette makes it possible to obtain a topsheet having a cloth-like soft feeling as well as a less glossy appearance and provided with liquid passages, the melt blown nonwoven fabric is generally characterized by its relatively small fineness and correspondingly poor elasticity to compression, so the liquid passages are readily collapsed under the body pressure of the user, often with the lower openings of the liquid passages distorted and consequently the body fluids are apt to be prevented from being rapidly transferred toward the absorbent core.

Accordingly, it is an object of the invention to solve the problems as mentioned by constructing a topsheet from an upper sheet layer composed of melt blown nonwoven fibric and provided with liquid passages and a lower fibrous layer underlying the upper sheet layer.

SUMMARY OF THE INVENTION

The object set forth above is achieved, in accordance with the invention, by a topsheet of body fluid absorptive goods provided with liquid passages each extending therethrough from top to bottom, wherein said topsheet is formed by melt blown nonwoven fabric comprising an upper sheet layer having a weight per unit area of 10 to $100g/m^2$ and provided with said liquid passages, and a lower fibrous layer underlying said upper sheet layer and bonded to said upper sheet layer adjacent said liquid passages as well as adjacent lower openings thereof, said lower fibrous layer having a fineness of 1 to 10 deniers, a weight per unit area of 10 to $40g/m^2$ and a density of 0.01 to $0.1g/cm^3$.

The topsheet according to the invention allows the body fluids to be transferred rapidly into the absorbent core and offers a cloth-like feeling and appearance, since the topsheet comprises an upper sheet layer made of melt blown nonwoven fabric provided with liquid passages and a lower fibrous layer bonded to the upper sheet layer in order to stabilize the configuration of the liquid passages so that these liquid passages do not easily collapse and the lower openings of these liquid passages are not significantly distorted.

BRIEF DESCRIPTION OF THE DRAWINGS

The invention will be described by way of example in reference with the accompanying drawings, in which.

DESCRIPTION OF THE PREFERRED EMBODIMENTS

Figure 1:
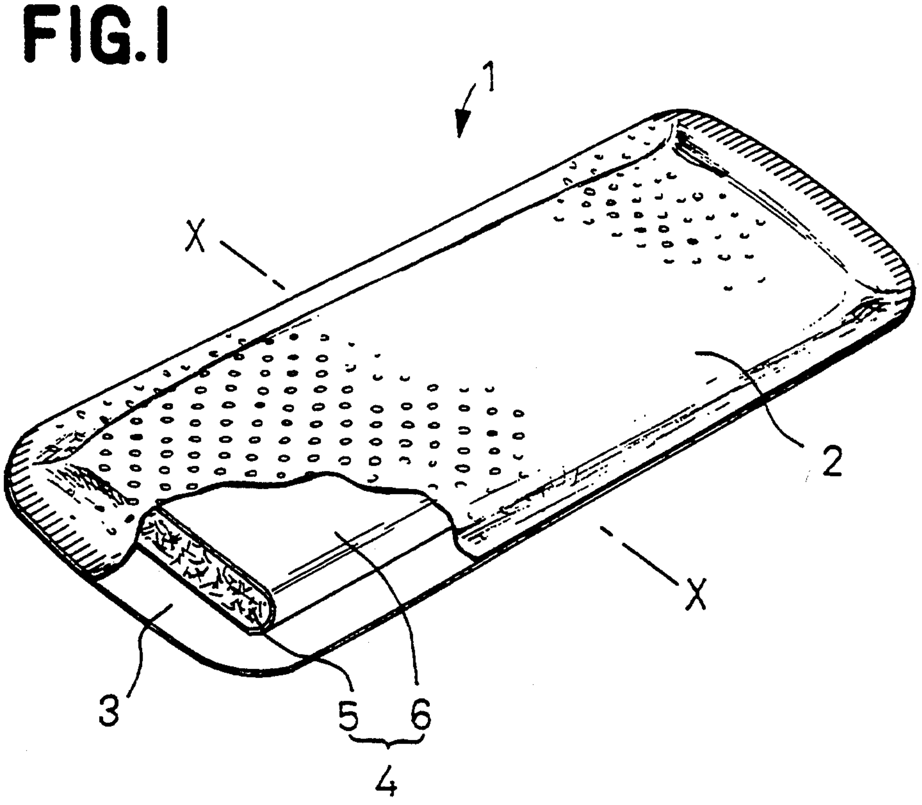
FIG. 1 is a perspective view partially broken away showing, a sanitary napkin employing a topsheet of the invention.

Referring to FIG. 1, a sanitary napkin 1 employing a topsheet 2 of the invention is shown in a perspective view as partially broken away. The sanitary napkin 1 comprises, as shown, the liquid-permeable topsheet 2, a liquid-impermeable backsheet 3 and an absorbent core 4 sandwiched between these sheets 2, 3, wherein parts of said sheets 2, 3 extending outward beyond a peripheral edges of the absorbent core 4 are closely bonded together.

Figure 2:
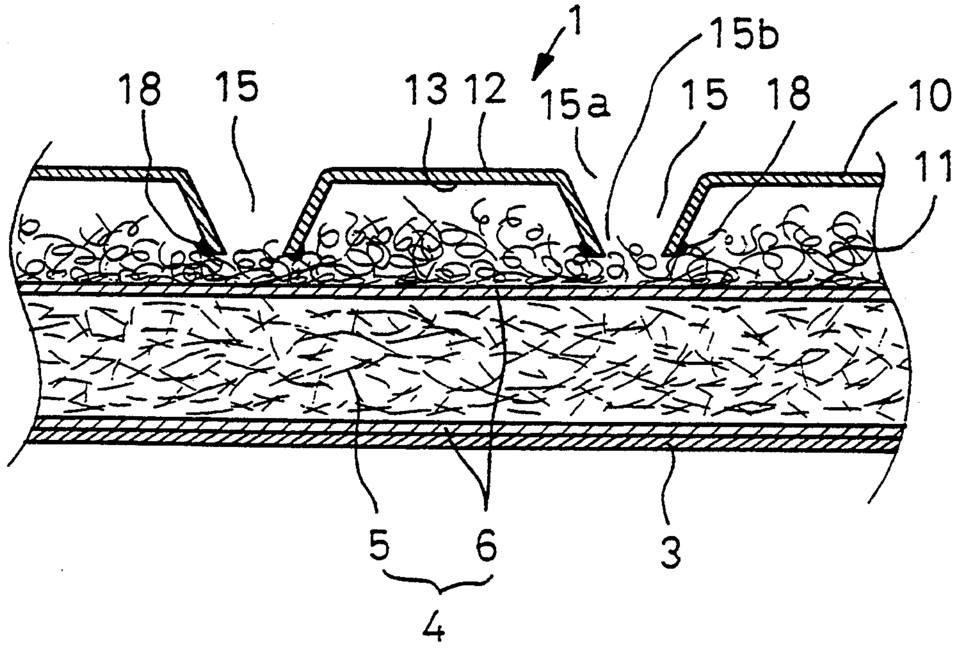
FIG. 2 is a sectional view as taken along a line X—X in FIG. 1, partially showing the sanitary napkin in an enlarged scale.

Referring to FIG. 2, the topsheet 2 is composed of an upper sheet layer 10 comprising thermoplastic fibres welded together and a lower fibrous layer 11 underlying said sheet 10 serving to provide the upper sheet layer 10 with a stiffness. The upper sheet layer 10 is formed with liquid passages 15 each extending therethrough from top 12 to bottom 13, and defining upper and lower openings 15*a*, 15*b*. These passages 15 make the sheet layer 10 liquid-permeable. The lower fibrous layer 11 covers the respective openings 15*b* also but to a degree maintaining the liquid-permeability of the sheet layer 11 and is bonded thereto with hot melt type adhesive at least adjacent the lower openings 15*b* of some of said liquid passages 15. The lower fibrous layer 11 serves to provide the upper sheet layer 10 with an elasticity to compression and thereby to reinforce the liquid passages 15 from the bottom side so that the liquid passages 15 may be effectively protected against collapse and the lower openings 15*b* of these passages 15 may be prevented from being distorted. In addition, the lower fibrous layer 11 lies in contact with the absorbent core 4 and helps the body fluids guided by the liquid passages 15 to be transferred into the absorbent core 4 under capillary action. The individual fibres of the lower fibrous layer 11 often partially get into the liquid passages 15 and such fibres also provide the capillary action serving to draw the body fluids into the absorbent core 4.

The upper sheet layer 10 may be made from melt blown nonwoven fabric having a weight per unit area of 10 to $100g/m^2$, for example, composed of olefin, polyester or polyamide thermoplastic fibres. Generally, the melt blown nonwoven fabric comprises fibres of relatively small deniers and makes it easily possible to provide a soft feeling as well as a less glossy appearance. The nonwoven fabric of this type can be made either air-permeable or air-impermeable depending on various factors such as the weight per unit area and whether the nonwoven fabric is subjected to the secondary heating treatment under a pressure or not. The melt blown nonwoven fabric may be used as material for the topsheet 10 whether it is air-permeable or air-impermeable. To provide the melt blown nonwoven fabric with the liquid passages 15, the method disclosed in Japanese patent application Disclosure Gazette No. 1991-51355 according to which melt blown fibres are blown against a mold plate having openings of a predetermined cross-sectional shape may be used as the process of manufacturing the nonwoven fabric and thereby the liquid passages 15 are formed. Lower ends of the respective liquid passages 15 present unevenness, i.e., indentation (irregularities) which may be left as is or neatly trimmed, if necessary.

The lower fibrous layer 11 may be formed by a popular thermoplastic fibre, for example, polyethylene or polypropylene fiber having a fineness of 1 to 10 deniers, a weight per unit area of 10 to $40g/m^2$ and a density of 0.01 to $0.1g/cm^3$. So far as the lower fibrous layer 11 can maintain its initial elasticity to compression even after it has been wetted with body fluids, the lower fibrous layer 11 may be mixed with some amount of a so-called sweat-absorptive synthetic resin composed of hydrophilic fibre such as rayon or polyester fibre having its surface made hydrophilic, and thereby transfer of the body fluids into the absorbent core 4 may be facilitated. If necessary, the lower fibrous layer 11 may be treated with a suitable hydrophilicity giving agent (surfactant).

Material for the lower fibrous layer 11 may also be selected from the group consisting of melt blown nonwoven fabric, melt bonded nonwoven fabric, binder bonded nonwoven fabric, water jetting fibre entangled nonwoven fabric and merely accumulated fibres capable of maintaining a desired sheet-like form. To hold the liquid passages 15 with a higher stability, there should be preferably available inter-fibre spaces allowing at least partially the lower ends of the respective liquid passages 15 to get into an upper portion of the lower fibrous layer 11. To bond the upper sheet layer 10 and the lower fibrous layer 11 together, these layers 10, 11 may be pressed against each other with hot melt adhesive 18 or the like applied to the upper sheet layer 10 around the respective openings **15*b* and to the lower fibrous layer 11. Alternatively, the material fibres used to form the upper sheet layer 10 and the lower fibrous layer 11**, respectively, may be welded together to achieve a similar bonding effect.

The liquid passages 15 are preferably dimensioned to have a diameter of 0.2 to 3 mm, more preferably of 0.7 to 2 mm at the upper opening **15*a*, a throat area ratio of 10 to 70%, a height of 0.3 to 5 mm and a diameter at the lower opening 15*b* equal to 30 to 200% of the diameter at the upper opening 15*a*. Such dimensioning is preferable not only to guide a stream of body fluids smoothly and rapidly into the absorbent core 4** but also to avoid a significant back flow thereof.

The liquid-impermeable backsheet 3 may be formed by a polyethylene sheet and the absorbent core 4 may be formed by a mixture of fluff pulp and superabsorptive polymer covered with tissue paper.

The topsheet of the invention allows the body fluids to be transferred rapidly into the absorbent core and offers a cloth-like feeling and appearance, since the topsheet comprises an upper sheet layer made of melt blown nonwoven fabric provided with liquid passages and a lower fibrous layer bonded to the upper sheet layer to stabilize the configuration of the liquid passages so that these liquid passages do not readily collapse and the lower openings of these liquid passages are not significantly distorted.

What is claimed is:

1. A topsheet (2) for body fluid absorptive articles comprising (a) an upper sheet layer (10) of melt blown nonwoven fabric having a weight per unit area of 10 to 100 $g/m^2$ and provided with a plurality of downwardly extending liquid passageways (15) having upper ends (**15*a*) and lower ends with lower openings (15*b*), and (b) a lower fibrous layer (11) underlying said upper sheet layer (10) having a fineness of 1 to 10 deniers, a weight per unit area of 10 to 40 $g/m^2$ and a density of 0.01 to 0.1 $g/cm^3$ the ends with lower openings (15*b*) of said downwardly extending passageways (15) being bonded to said lower layer (11) so as to protect said downwardly extending liquid passageways (15) against collapse and protect said lower openings (15*b***) from being distorted.

2. A topsheet (2) according to claim 1, wherein each of said liquid passageways (15) has a diameter of 0.2 to 3 mm at its upper opening (**15*a*), a throat area ratio of 10 to 70%, a height of 0.3 to 5 mm and a diameter at its lower openings (15*b*) equal to 30 to 200% of the diameter of said upper opening (15*a***).

3. A topsheet (2) according to claim 1, wherein said nonwoven fabric forming said upper sheet layer is only composed of hydrophobic synthetic fiber.

4. A topsheet (2) according to claim 1, wherein said lower fibrous layer (11) is composed only of hydrophilic synthetic fiber.

5. A topsheet (2) according to claim 1, wherein said lower fibrous layer (11) comprises (a) a hydrophilic synthetic fiber or (b) a synthetic fiber with its surface made hydrophilic or (c) a mixture of (a) and (b).

6. A topsheet (2) according to claim 1, wherein said lower fibrous layer (11) has been treated with a suitable hydrophilicity providing agent.

* * * * *